United States Patent [19]
Jeng

[11] Patent Number: 6,139,507
[45] Date of Patent: Oct. 31, 2000

[54] METHOD AND APPARATUS FOR MEASURING ACOUSTIC POWER FLOW WITHIN AN EAR CANAL

[75] Inventor: Patricia S. Jeng, Mountainside, N.J.

[73] Assignee: Miomsa Acoustics Inc., Mountainside, N.J.

[21] Appl. No.: 09/230,661

[22] PCT Filed: Aug. 12, 1997

[86] PCT No.: PCT/US97/13953

§ 371 Date: Jan. 29, 1999

§ 102(e) Date: Jan. 29, 1999

[87] PCT Pub. No.: WO98/06324

PCT Pub. Date: Feb. 19, 1998

Related U.S. Application Data

[60] Provisional application No. 60/023,834, Aug. 12, 1996.

[51] Int. Cl.[7] .................................................... A61B 5/00
[52] U.S. Cl. ............................................ 600/559; 73/585
[58] Field of Search ................................ 600/559; 73/585

[56] References Cited

U.S. PATENT DOCUMENTS

| | | | |
|---|---|---|---|
| 5,105,822 | 4/1992 | Stevens et al. | 600/558 |
| 5,197,332 | 3/1993 | Shenib | 73/585 |
| 5,526,819 | 6/1996 | Lonsbury-Martin | 364/413.02 |

OTHER PUBLICATIONS

Voss and Allen, Measurement of Acoustic Impedance and Reflectance in the Human Ear Canal, J.Acoust.Soc.Am 95(1), Jan. 1994.

*Primary Examiner*—Cary O'Connor
*Assistant Examiner*—Pamela Wingood
*Attorney, Agent, or Firm*—Woodbridge & Associates, P.C.; Richard C. Woodbridge; Stuart H. Nissim

[57] ABSTRACT

A system and method for accurately determining the power flow within a test subject's ear canal. A calibration device (300) is used in conjunction with a probe device (400) that measures the frequency response of a cavity. The probe (400), with eartip (440), is inserted into a patient's ear and a transducer (460,470) emits a periodic signal into the ear canal. The transducer (460,470) also measures the frequency response of the ear canal and relays the data back to a digital signal processor. The same probe setup (400) is then calibrated by measuring the frequency response of a plurality of cavities (340*a*, 340*b*, 350*c*, 350*d*) having known geometries. Mean cavity length is solved for based upon the known geometries of the plurality of cavities. Consideration is also given to spreading mass wave phenomena due to point source transducer emission. Cavity temperature for calibration purposes is maintained as close as possible to body temperature thereby negating a farther source of error. Several measurements, including cavity impedance and pressure reflectance, are calculated from the frequency response data obtained. This data, in turn, yields valuable diagnostic information for determining ear pathologies in humans. The method and apparatus of the present invention is quick, easy, and efficient thereby lending itself to clinical use.

17 Claims, 9 Drawing Sheets

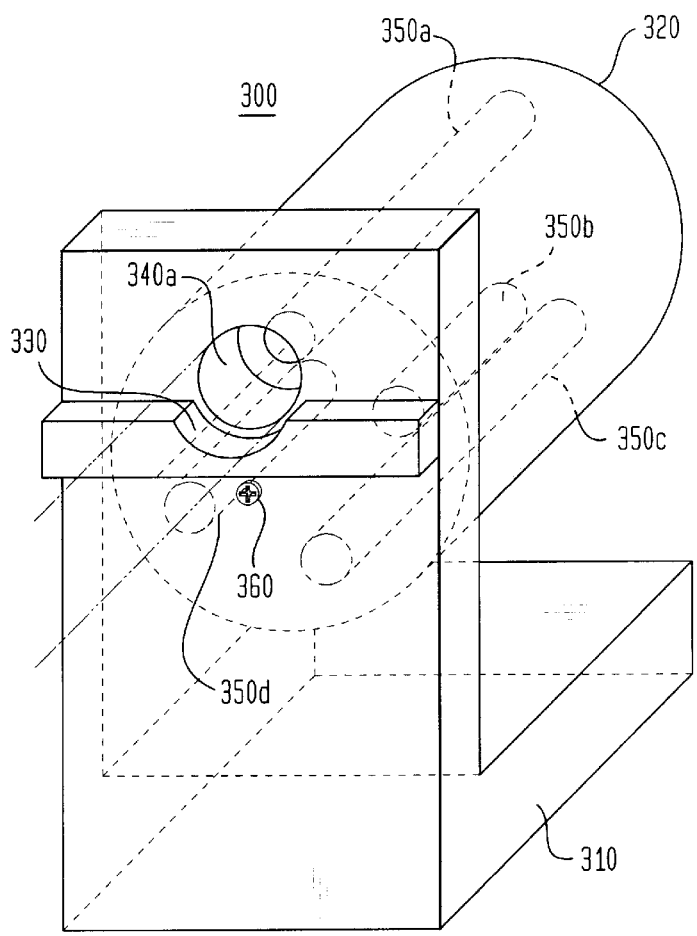
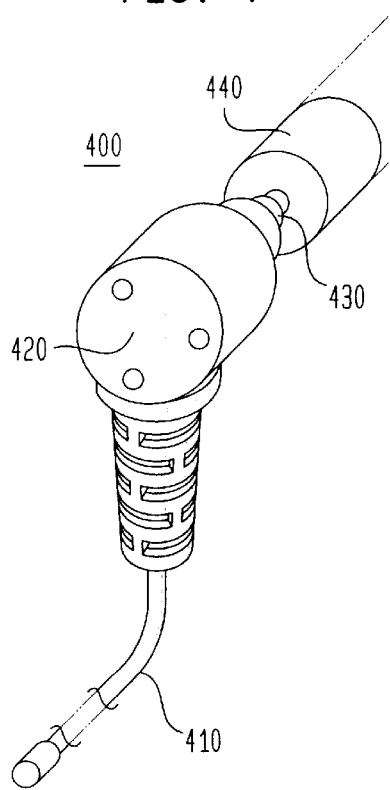

METHOD AND APPARATUS FOR MEASURING ACOUSTIC POWER FLOW WITHIN AN EAR CANAL

CROSS-REFERENCE TO RELATED APPLICATIONS

This application is related to and claims the benefit of U.S. provisional application No. 60/023,834 filed Aug. 12, 1996 entitled "METHOD AND APPARATUS FOR MEASURING THE ACOUSTIC POWER FLOW WITHIN THE EAR CANAL" the entire contents of which are incorporated herein by reference.

BACKGROUND OF THE INVENTION

1. Field of the Invention

The present invention is directed toward a system and apparatus for accurately and rapidly measuring acoustic power flow at various points within the human ear canal.

2. Description of Related Art

In the field of audiology the chief objective of most diagnostic tools is to obtain an accurate measurement of wide band, middle ear power flow as estimated from the ear canal power flow. Power flow per unit area is known as acoustic intensity. An accurate reading of acoustic intensity is necessary for improved clinical diagnosis with respect to pathologies of the human auditory system. Accuracy alone, however, is insufficient to provide a clinically acceptable diagnostic system. The measurements must be obtainable rapidly and in a cost-efficient manner. Thus, the goal of the present invention is to provide a cost efficient, rapid, and accurate system of obtaining an acoustic intensity measurement within the human auditory system. Such a system will provide, inter alia, significant benefits in hearing screening programs leading to earlier discovery of ear pathologies.

Diagnostic tools such as air conduction audiometry, bone conduction audiometry, evoked response audiometry, and evoked otoacoustic emissions are critically dependent on an accurate measurement of the acoustic sound field. More specifically, acoustic intensity is a desirable measurement. Acoustic intensity is a measurement of the power flow per unit area. Unfortunately, measuring intensity directly is extremely difficult.

A more easily obtainable measurement is that of sound pressure as opposed to acoustic intensity. Pressure instruments are widely used in audiology. Pressure, however, only yields an intensity estimate when no standing waves are present, i.e., when power is flowing in one direction only, namely in sound fields that do not have acoustic reflection components. In sound fields having acoustic reflection components, standing waves will be produced and a pressure measurement is ineffective.

When reflections are not present, power flow is proportional to the square of the pressure multiplied by the area along the ear canal. In a calibrated pressure field having no reflection, power can be independent of frequency. However, when reflections are present in the ear canal then canal impedance is a finction of location in the ear canal, even if the pressure field is calibrated. In this case the square of the pressure does not characterize power flow. Sound pressure and acoustic intensity have a complex relationship when reflections are present in the ear canal. Thus, a single pressure measurement cannot determine the acoustic power flow in the ear canal unless the source transducer has been characterized. The source transducer is a small loud speaker/receiver combination placed in the ear canal. At least two independent measurements are necessary to do this. Characterization requires determining the source transducer's open-circuit pressure and its source impedance. Use of pressure as a measure of signal strength does not, however, take into consideration the source transducer open-circuit pressure or the source transducer impedance and thus cannot determine actual acoustic intensity in an ear canal having standing waves due to reflection.

In the early days of audiometry (circa 1930), sound levels were calibrated in a free-field (i.e. a field free of standing waves) where sound pressure and acoustic intensity are equivalent. Supra-aural headphones soon became popular because of their increased ease of use, acoustic isolation, and reduced low frequency calibration variability. These headphones were typically calibrated with a standardized acoustic coupler (i.e., artificial ear). This method of calibration improperly assumed that the acoustic impedance of the coupler was essentially the same as that of the ear being tested. As a result, considerable difficulty was encountered in developing a practical, yet reasonable way of accurately specifying hearing loss. One practical problem that emerged in defining the "normal threshold of hearing" was that different values for the auditory threshold were obtained on the same subject using different audiometric headphones, such as the American TDH-39 and the British STL headphones, although both headphones were calibrated on the same standard coupler.

A practical compromise was reached in 1969 with the standardization of the *International Standard Reference Zero* for audiometers. This standard is now universally accepted. In order to measure hearing level it is necessary to used a standard headphone calibrated in a standard coupler. A correction factor is needed if a transducer or coupler other than the standard headphone-coupler pair is used.

The above approach to the measurement of hearing level represents a practical compromise that works only moderately well below 4 kHz for normal adult ears. The approach remains, however, cumbersome and prone to error. Two important sources of error include inter-subject variability in the acoustic impedance of the tympanic membrane and in the cross-sectional area of the ear canal, and standing waves in the ear canal which result from an impedance mismatch between the tympanic membrane impedance and the ear canal characteristic impedance. These errors are sufficiently large above 4 kHz so as to render this method unusable.

The above sources of error are of particular concern when measuring hearing levels in infants and children because of the smaller physical size of their ear canals and the difference in acoustic impedance from that of the average normal adult ear. Similarly, the measurement of hearing levels in the presence of middle-ear pathology can also lead to error because acoustic impedance of the middle-ear is likely to deviate substantially from that of a normal ear. These two sources of error are often compounded in pediatric audiology because of a high incidence of otitis media in children.

A related problem is measuring acoustic signal levels produced by a hearing aid. The presence of an ear mold or an in-the-canal hearing aid results in a substantial change to the sound field within the ear canal. Under these conditions the predicted ear canal sound pressure level measured by a coupler can be very misleading.

Given the limits of current technology, one approach to this problem has been to increase the accuracy of the determination of the pressure not the intensity in the ear canal. For example, within the past ten years "real ear" measurement systems have become popular. These systems estimate the pressure in the ear canal in an attempt to lessen the uncertainty between a standard coupler and the ear being tested. When standing waves are present, however, pressure in the ear canal away from the tympanic membrane is not the same as the tympanic membrane pressure, nor does it characterize the acoustic power flow in the ear canal (i.e. the true intensity).

In the last five to ten years, evoked otoacoustic emissions, such as distortion products, have proven to be an important new method for characterizing the outer hair cell finction in the cochlear. Distortion product evoked otoacoustic emissions are small nonlinear cochlear retrograde signals. While this nonlinear measurement represents an important positive step in diagnosing hearing loss, it is also affected by standing waves due to middle ear reflections. When a calibration microphone is in a primary pressure null, created by a reflected (retrograde) pressure wave that partially cancels the forward traveling wave, the pressure at the measurement point and at the ear drum can differ by an arbitrarily large amount. Recently, 20 dB standing waves in adult ears sealed with an insertion—transducer have been observed at frequencies as low as 3.5 kHz. Under these conditions the ear canal acoustic intensity is not properly calibrated. Since distortion product evoked otoacoustic emission and other clinical measures depend on stimulus intensity the reliability of the calibration is critical.

This problem is exacerbated in cases of neonates and infants due to vemex in the canal within the first few days after birth, and middle-ear infections in infants and young children.

In all of these cases a significant percentage of the acoustic energy may be reflected by the middle-ear due to pathological middle-ear impedance mismatch.

The practical consequences of this impedance mismatch problem are substantial. Consider, for instance, a universal hearing screening program for infants. For every 1000 infants screened, we might expect only two or three to be cochlear-impaired (i.e. 0.2–0.3% of the population), and 50 to 100 (5–10%) to have some sort of middle-ear pathology (usually temporary). Both of these groups will test positive in an evoked otoacoustic emissions screening program. The middle-ear "positives" represent a large group of false-positives, with respect to cochlear pathology, that need to be identified. This is because the next stage of the process is to evaluate all positive cases using a much more time consuming and costly procedure, such as behavioral testing and/or Auditory Brainstem Evoked Response Audiometry (ABER).

The use of evoked otoacoustic emissions as a screening tool is growing rapidly because of the speed, ease of testing and objectivity of this technique. In order for a screening program using evoked otoacoustic emissions to be cost effective it is essential that the high rate of false positives with respect to cochlear pathology due to middle-ear problems be reduced substantially. An effective solution to this problem would be to separate cochlear "positives" from middle-ear "positives" during the evoked otoacoustic emissions screening stage and to initiate appropriate forms of evaluation and intervention for each of these cases.

All of the problems described above can either be totally eliminated, or at least reduced considerably, if we knew the acoustic power flow in the ear canal. In addition to these advantages there are other, more subtle considerations for developing an instrument capable of measuring acoustic power flow in the ear canal.

In the normal human middle ear, the ear canal and middle-ear impedances are substantially matched for frequencies above 800 Hz, allowing for efficient power flow from the ear canal to the cochlea. Ear drum impedance will change when the middle-ear malfunctions, for example due to static pressure in the middle-ear space, or under more serious conditions such as changes in the ossicular impedance due to otospongiosis (otosclerosis), or changes in the stiffness of the ossicular ligaments. When impedance mismatch is large, power reflectance approaches 1 (i.e., 100% of the power is reflected). Under this condition output acoustic intensity is nearly equal to the input acoustic intensity, and the forward and retrograde waves are almost equal in magnitude. As a result, the pressure nearly cancels at frequencies corresponding to ¼ acoustic wavelengths or ½ wavelength round trips from the reflection point. Pressure will be very small at the measurement point for this frequency yielding a misleading pressure calibration since the ear canal pressure at the measurement point for this frequency is not a useful or accurate measure of either drum pressure or the power absorbed by the middle-ear and cochlea.

Measuring the power absorbed by the middle ear and cochlea provides many advantages in audiology, particularly when at frequencies above 4 kHz where there is a middle-ear pathology, or when the physical size of the ear is very different from the normal adult ear. This is typical in cases where traditional coupler measurements provide misleading estimates of the sound pressure level at the eardrum. Three important observations have been derived for normal ears. First, middle-ear impedance mismatch is a large source of variability from human to human. Second, a cat's middle ear is nearly a lossless system. Third, power flux at the threshold of hearing in a gerbil has been found to be constant.

The first observation identifies a significant physical source of calibration variability. The second observation means that virtually all of the power flowing into the middle ear is delivered to the cochlea. The third observation is consistent with the idea that acoustic power flow is an important correlate of cochlear hearing thresholds.

In order to measure power absorbed by the middle ear it is necessary to measure the acoustic impedance of the middle-ear. Instruments in current clinical use for measuring acoustic impedance of the ear, however, do not measure acoustic impedance directly, but rather measure the relative impedance magnitude, i.e., the impedance magnitude relative to that for a normal ear. These instruments are also frequently limited to a few standard test frequencies (e.g., 220 Hz and 600 Hz), rather than providing a measurement of acoustic impedance over the entire audio frequency range.

Recent advances in transducer development and concomitant advances in computerized measurement of sound transmission characteristics in the ear allow for a practical means of measuring acoustic impedance, and more importantly, sound power absorption by the ear. The instrument of the present invention is a significant improvement over a technique developed by Jont B. Allen, "Measurement of Eardrum Acoustic Impedance", *Peripheral Auditory Mechanism*, pp. 44–51 (1986). In Allen's methodology two transducers are inserted into the ear canal. One transducer generates a test sound, the other, a microphone, measures the pressure in the test ear. The two transducers are then placed in four cavities, where the cavity pressures are measured. This information is then analyzed to produce an estimate of the canal reflectance. The above described measurement method has been applied to animals, adults, temporal bones, and infants. The instrumentation used in Allen's experiments, however, is expensive and complex and is therefore not amenable to use in a clinical setting.

SUMMARY

The purpose of the present invention is to provide a simple device for the measurement of acoustic intensity in a subject's ear canal. The invention comprises signal generation means, a probe device having an earphone/microphone connected to the signal generation means, and a plurality of calibration cavities of known impedance which are a function of an unknown average length. The probe is inserted into the subject's ear canal and the signal generation means via the earphone emits a periodic signal into the subject's ear canal. The pressure response of the ear canal is measured and recorded. The calibration cavities have their pressure responses measured and the probe is calibrated by computing the calibration responses and searching, i.e. solving for, the unknown average cavity length. A basic assumption of the calibration method is the linearity of the probe device being calibrated. Then, from the pressure response of the subject's ear canal, the acoustic impedance and intensity in the ear canal may be estimated. The method and apparatus of the present invention is intended for a clinical setting requiring minimal training. Once the subject's acoustic power flow has been estimated, ear pathologies can be detected and treatment recommended. Early detection of ear pathologies also help reduce further ear damage.

BRIEF DESCRIPTION OF THE DRAWINGS

FIG. 3 illustrates a calibration device according to the preferred embodiment of the invention.

FIG. 4 illustrates a probe device according to the preferred embodiment of the invention.

DETAILED DESCRIPTION

Like numbers will be used to describe like elements as shown on the various figures which describe the invention.

Experiments have been conducted pertaining to acoustic ear canal impedance and reflectance measurements from 0.1 to 15.0 kHz for ten human subjects having normal hearing. The results of these experiments were memorialized by the Acoustical Society of America in a paper by Susan E. Voss and Jont B. Allen entitled "MEASUREMENT OF ACOUSTIC IMPEDANCE AND REFLECTANCE IN THE HUMAN EAR CANAL" 95 J. Acoust. Soc. Am. 372 (Jan. 1994).

Figure 1:
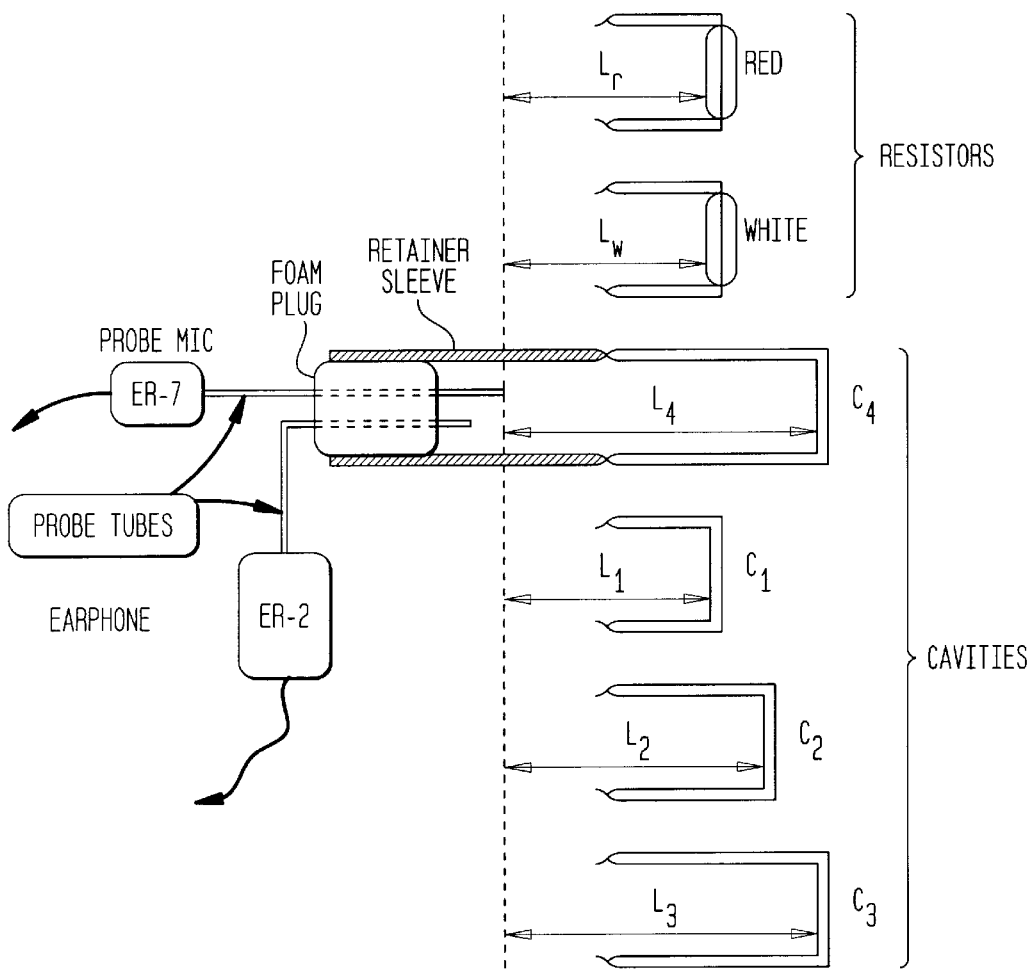
FIG. 1 illustrates a prior art calibration setup for measuring the Thevinin parameters of an earphone.
Figure 2:
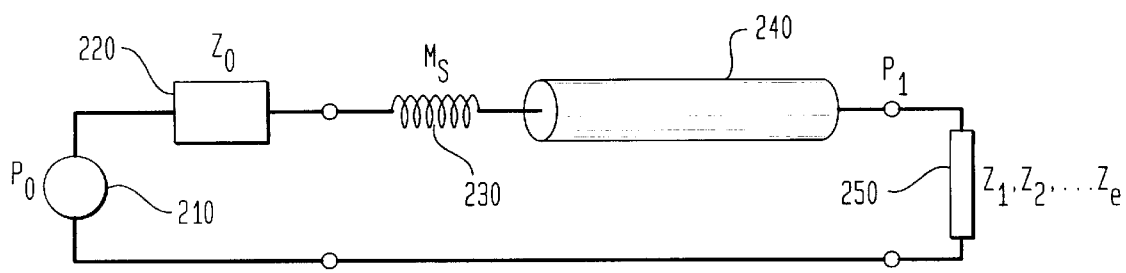
FIG. 2 illustrates an equivalent electrical circuit showing the spreading mass $M_s$ without the spreading mass term the circuit models the prior art setup of FIG. 1.

An acoustic transducer package, shown in prior art FIG. 1, consists of an earphone and microphone terminated in a foam ear tip. To measure an ear-canal acoustic impedance $Z_e(f)$ the transducer package must first be calibrated. This means measuring the Thevenin parameters (FIG. 2), the open-circuit source pressure $P_0(f)$, and the source impedance $Z_0(f)$. Once the Thevenin parameters are known, the desired ear canal impedance $Z_e$ may be determined from a measurement of the ear canal pressure $P_e$. From any two cavity pressure measurements $P_1 f$ and $P_2(f)$, the two Thevenin parameters $P_0$ and $Z_0$ may be calculated if the corresponding cavity lengths are known. The problem is that the acoustic lengths, which depend on the spreading of the wave as shown in FIG. 10, are not accurately known.

The acoustic properties of the cavities depend on their length and area. The area is fixed, and is the same for all the cavities, and is equal to the average area of the human ear canal. When infants are measured, the average area of an average infant ear canal should be used.

Figure 6:
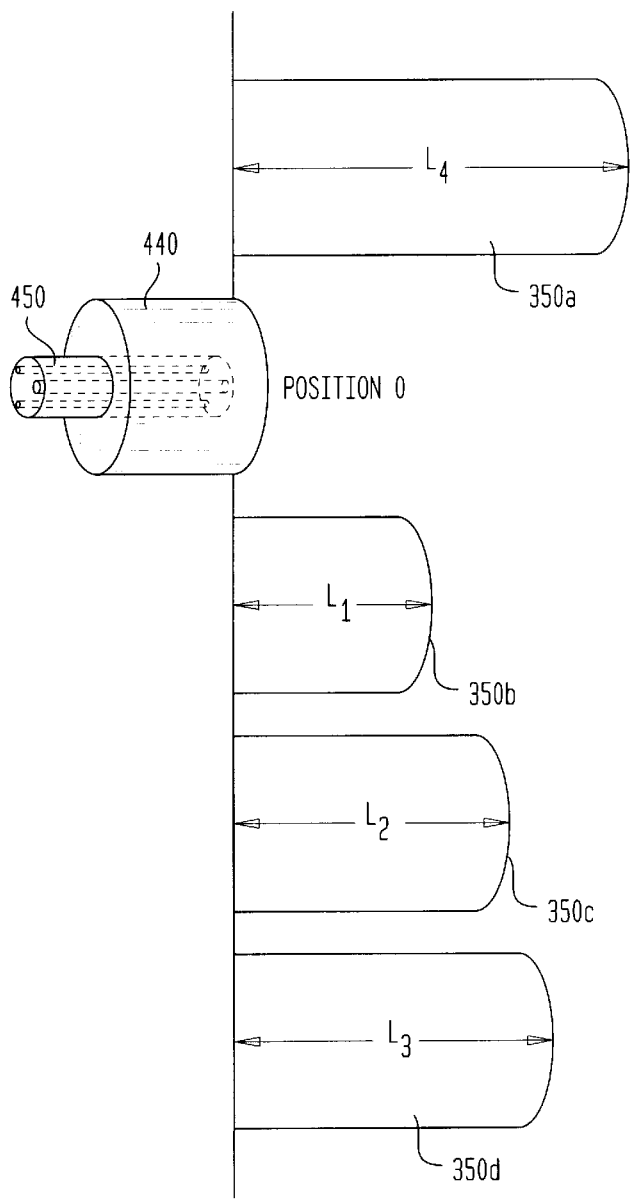

As shown in FIG. 1 and FIG. 6, the four physical cavity lengths $L_i$, i=1,2,3,4, are defined from the reference plane [typically the same as the tip of the probe microphone orifice FIG. 6, POSITION 0)], to the distal end of each cavity.

Figure 10:
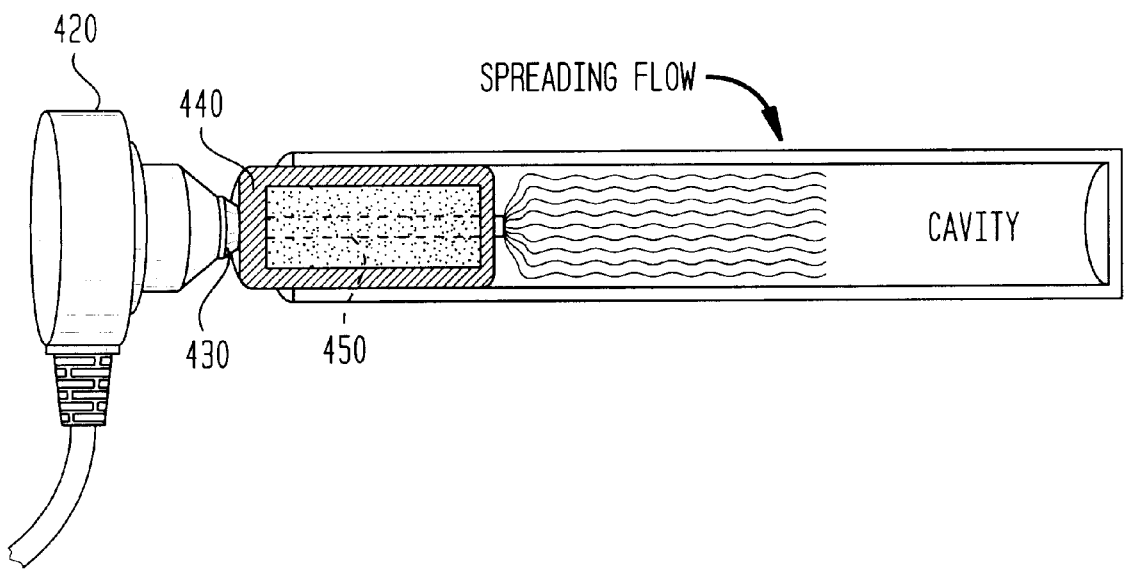
FIG. 10 illustrates the flow of sound from a point source within a cavity, such as the ear canal.

As may be seen from FIG. 10 the acoustic flow spreads from the sound outlet orifice and the length traveled is greater than the actual physical distance from the outlet orifice to the end of the cavity tube.

The acoustic length differs from the physical length $L_i$. The difference between the acoustic and physical lengths is defined as $\Delta_0(f)$, which is a function of frequency but is independent of the cavity number i. Thus the acoustic length $\mathcal{L}_i$ of the $i^{th}$ cavity is $$\mathcal{L}_i = \Delta_0(f) + L_i$$

The physical properties of $\Delta_0(f)$ are accounted for by the spreading inertance $M_s$ (230), referred to in the acoustics literature as a spreading inertance. $M_s$ is a function in the change in area at the probe tip.

Mass $M_s$ represented in the electrical equivalent acoustic circuit (FIG. 2) as an inductor in series with the earphone (420) transducer orifice. Thus the magnitude of this mass is unknown for each condition and must be treated as an unknown parameter. The recognition of the importance of this acoustic mass to the accuracy of the calibration is an important element of the present invention.

By taking the difference between the acoustic lengths of any two cavities, because $\Delta_0(f)$ is independent of the cavity index, the acoustic path difference $\Delta_0(f)$ cancels, namely $$\mathcal{L}_i - \mathcal{L}_j = L_i - L_j$$

The cancellation of $\Delta_0(f)$ reduces the gradient search from four dimensions to one dimension, because these differences are accurately known.

This greatly simplifies the method of finding the acoustic lengths, and is an important feature of the present invention.

In practice, the foam eartip (440) is never inserted to exactly the same depth during a calibration. Thus there are two important sources of error in determining the length L, (1) the difference between the acoustic length and the physical length [$\Delta_0(f)$], and (2) the insertion depth variability.

To define a reference point that is neutral to all these definitions, we define the mean physical cavity length $L_0$ as $$L_0 \equiv \frac{1}{N}\sum_{i=1}^{N} L_i$$

and the mean acoustic cavity length $L_0$ as $$\mathcal{L}_0 \equiv \frac{1}{N}\sum_{i=1}^{N} \mathcal{L}_i$$

where $2 \leq N \leq 6$ is the typical number of cavities used in practice. Using these definitions we define the differences $\Delta_i$, which are accurately known, as $$\Delta_i = L_i - L_0 = \mathcal{L}_i - \mathcal{L}_0.$$

As before, we have used the fact that $\Delta_0(f)$ cancels when computing differences.

Even though the basic equations for the Thevenin parameters are linear, the mathematical search space for the cavity lengths ($\Delta_i = L_i - L_0$) and the spreading mass ($M_S$) are non-linear. This leads to an error surface having many local minima, and a non unique solution. Multiple dimensional searches are known to be problematic. A constraint on the differential cavity lengths ($\Delta_i = L_i - L_0$), which reduces the search for the length to one dimension, simplifies the problem and leads to a unique global minimum solution. The spreading mass ($M_S$) effectively accounts for $\Delta_0(f)$ frequency dependent length difference of the cavity that must be accounted for if the Thevenin parameters are to be an accurate representation over a large range of frequencies. Since the magnitude of this spreading mass ($M_S$) depends on the geometry of the probe and the geometry of the ear canal, it is not possible to know the magnitude of the spreading mass ($M_S$) in advance.

In summary, when searching for the acoustic lengths, the new cavity model has two degrees of freedom, the mean acoustic length $\mathcal{L}_0$ and the spreading inertance, $M_s$. As described above, typically, in the prior art, four acoustic cavity lengths $\mathcal{L}_i$ were the search parameters, and the spreading inertance effect was ignored. Thus, the present invention has reduced the search from four to two dimensions, and improved the cavity model.

The present invention greatly enhances the accuracy and utility of the calibration method introduced by Allen in 1986 and described in Voss and Allen, "MEASUREMENT OF ACOUSTIC IMPEDANCE AND REFLECTANCE IN THE HUMAN EAR CANAL". 95 *J. Acoust. Soc. Am.* 372 (Jan. 1994), by recognizing that the spreading mass ($M_s$) is well represented by a single parameter which can be estimated using the same search method used to determine the mean acoustic cavity length ($\mathcal{L}_0$), and by recognizing that the differential lengths, $\Delta_i = L_i - L_0$, are known and are not a function of the depth of insertion of the earphone into the measurement cavities.

There are three important extensions to the method described in Voss and Allen which comprise the substance of the present invention. First, defining the search for mean acoustic cavity length reduces the search from a four dimensional search to a one dimensional search. Second, the effect of higher order modes near the sound outlet is compensated for by searching for the spreading mass. Lastly, the cavities are maintained at the same temperature as the ear canal (i.e. body temperature) rather than at room temperature.

In Voss and Allen's previous prior art experiments, each of ten subjects had their ear canal impedance measured. This measurement consisted of seven complex frequency responses, namely, four sealed cavities, two resistor cavities, and the subject's ear. (See FIG. 1). Each individual pressure frequency response measurement took 2.6 seconds. Four acoustic lengths, $\mathcal{L}_1$ to $\mathcal{L}_4$, for the four cavities were computed from the measured cavity pressures using a least squares gradient procedure. Cavity impedances were calculated using acoustic lossy-transmission line equations. At each frequency, two earphone Thévenin parameters, source impedance $Z_s(\omega)$ and open circuit pressure $P_s(\omega)$, or their Norton equivalents, $Y_s(\omega)$ and $U_s(\omega)$, were found from the four measured cavity pressures and computed cavity load impedances once the acoustic lengths were determined. Calibration was verified by determining the impedance of two acoustic resistors from the two resistor pressures. If the measured resistor reflectances were within a tolerance range, then the subject's ear canal impedance was computed from the measured canal pressure. If not, the calibration and measurements were repeated. Thus, the resistors served as a control on the calibration.

The Allen/Voss method relies upon knowing and using the lengths of each of the cavities. This constitutes a four dimensional search space. The present invention reduces this search space to one dimension. This reduction is possible because the difference in lengths among the four cavities, when taken in pairs, is known and may be precisely controlled. This is true even though the absolute lengths from the tip of the probe microphone to the ends of the cavities are not known. For example, $\Delta_i$ is known even though $\mathcal{L}_i$ is unknown. This is because the mean inserted depth of the eartip into the cavities is not precisely controllable. Thus, the search for the cavity lengths may be constrained to the search for one length, such as the length of the shortest cavity of the four cavities. The number of cavities used for calibration may be varied. An increased number of cavities does provide a more accurate length measurement, but it requires an excessive amount of time. Experimental results have shown four cavity lengths to be a reasonable compromise between accuracy and the time required to obtain the measurement.

The second extension of the Allen/Voss methodology corrects for the effect of the spreading of the sound near the sound outlet. FIG. 10 shows how sound disperses throughout the ear canal due to a sound point source orifice. The spreading of the acoustic waves may be treated as a spreading mass term $M_s$, described in FIG. 2, which is added to the cavity impedance. It is possible to estimate this unknown mass term by searching for it, just as the unknown mean acoustic cavity length $\mathcal{L}_0$ is searched for, minimizing the residual error in the over-specified Thevenin equations. Adding the unknown parameter $M_s$ results in a two dimensional search space (i.e., $\mathcal{L}_0$, and $M_s$). After "converging" the two dimensional search for the spreading Mass $M_s$ and the overall length $\mathcal{L}_0$ and assuming known differential lengths, an optional final search in all five dimensions, ($\mathcal{L}_1, \mathcal{L}_2, \mathcal{L}_3, \mathcal{L}_4$, and $M_s$), may be made to determine the true local minimum.

The spreading mass ($M_s$) effectively introduces a frequency dependent length of the cavity, and therefore must be accounted for when measuring over a large range of frequencies. Since the magnitude of this mass depends on the geometry of the probe and the ear canal, it is not possible to know its magnitude in advance. By recognizing that the magnitude is well represented by a single parameter that can be estimated by the same search method used to recover cavity lengths, we greatly enhance the accuracy and utility of the calibration method.

The third extension requires maintaining the cavities at the same temperature as the ear canal. Previously, the cavities were at room temperature while the ear canal was at or near body temperature. Consequently, a small frequency dependent error was introduced in the open circuit pressure and the Thévenin source impedance. By maintaining the cavities at body temperature these errors can be eliminated by reducing the unwanted frequency artifacts. The Thevenin parameters can also be corrected for changes in the temperature of the transducer by scaling the speed of sound in the sound delivery tube by the square root of the temperature.

FIG. 3 illustrates a calibration device 300 according to the preferred embodiment of the invention. The calibration device 300 is an L-shaped base and stand 310 having a cylinder 320 rotatably connected to and extending away from stand 310.

Cylinder 320 has four cavities which extend into the cylinder 320 as well as a zero position, $L_0$. Each cavity extends a different length ($L_1$, $L_2$, $L_3$, $L_4$) into the cylinder 320 thereby providing each cavity with a different geometry. The zero position does not extend into cylinder 320. Rather, it prevents the probe/earphone combination from being inserted too deeply within the calibration device. Once inserted to the right depth, the cylinder is rotated to each cavity and measurements are taken. The cavities end in a hard wall or in a known acoustic impedance.

Stand 310 has a circular bore 340a equal in size to the diameter of the four cavities. Cylinder 320 is connected to stand 310 via a screw that runs the entire length of the cylinder's 320 axis into and through the front face of the stand 310 such that the cylinder is flush against the back of the stand and is able to rotate about its own axis. A probe head rest bar 330 extends across the face of stand 310 and has a cut out semi-circular shaped portion for receiving a probe head. The cut out portion is aligned with circular bore 340a.

Figure 5:
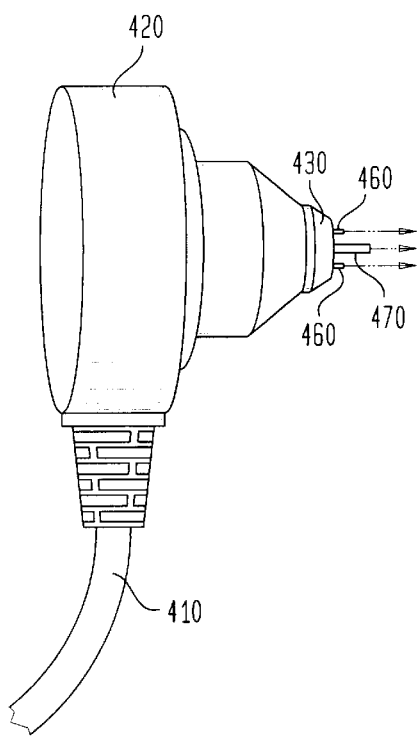
FIGS. 5 and 6 illustrate the probe device according to the preferred embodiment of the invention including the probe tip.

FIG. 4 illustrates a probe device 400 used in conjunction with the calibration device 300 of FIG. 3. Probe device 400 comprises a probe cable that is connected to a digital signal processor (DSP) on one end and a probe head 420 on its other end. Probe head 420 is cylindrically shaped and is designed to fit snugly into the cut out portion of probe head rest bar 330. Referring to FIGS. 5 and 6, probe head 420 tapers into a probe tip 430. Probe tip 430 terminates with a pair of receiver tubes 460 and a microphone tube 470. An eartip 440 having a sound delivery tube 450 attaches to probe tip 430. Sound delivery tube 450 extends longitudinally through the entire length of 440 and has three receptacles for receiving both receiver tubes 460 and microphone tube 470.

Figure 15:
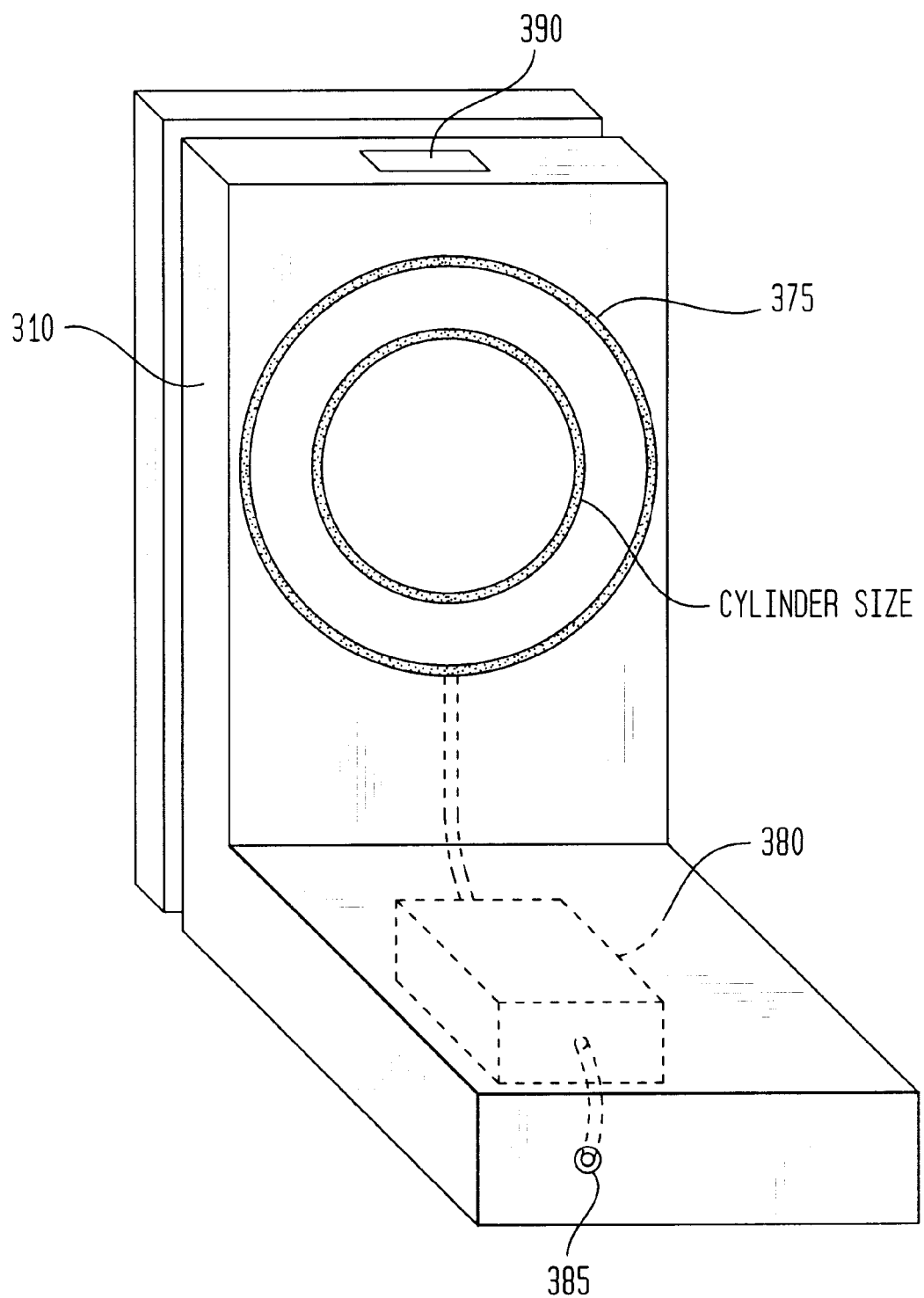
FIG. 15 illustrates a back view of FIG. 11 with the cylinder removed and also shows the heating element system used to maintain the cavities at constant body temperature.

In order to maintain the cavities of the calibration device at body temperature rather than room temperature, small circular heating elements 375 are embedded in the vertical part of stand 310 as depicted in FIG. 15. This allows heat to propagate to cylinder 320 in an even manner avoiding heat pockets. These heating elements 375 are electrically driven by a plug adapter 385 into the calibration device 300. Cavity temperature is continually monitored by a temperature feedback servo-mechanism 380 embedded in stand 310 for maintaining the cavities at normal body temperature. A temperature display 390 may also be included to inform the operator of the current cavity temperature.

Figure 7:
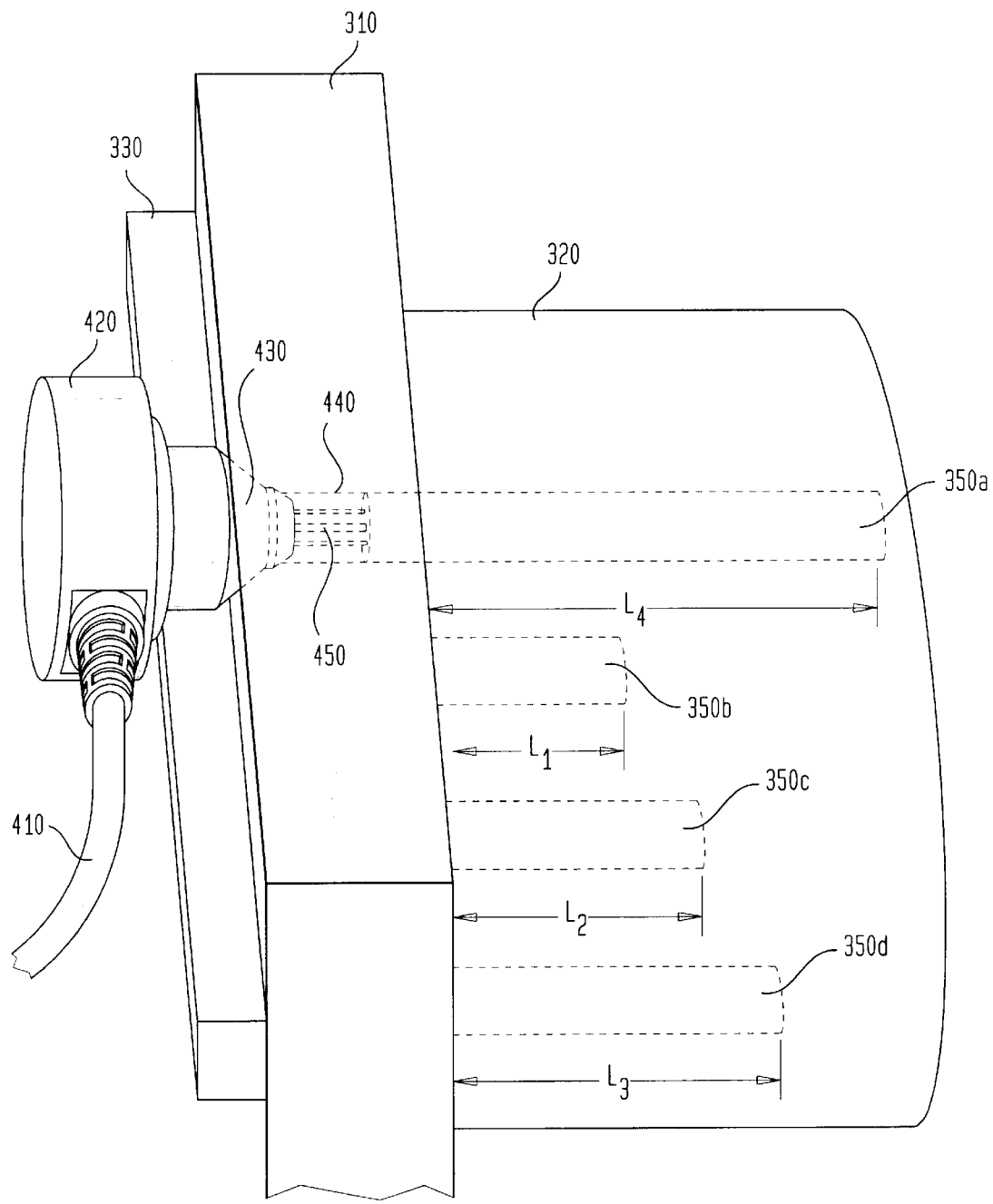
FIG. 7 illustrates the probe and calibration device during calibration of a cavity.

Once an eartip 440 with foam tip has been fitted to probe tip 430 the entire probe device is ready to be used. It can be used to measure the frequency response of a human ear canal by inserting the eartip into a patient's ear and delivering a periodic signal into the ear canal which is recorded and analyzed. It can also be used to measure the frequency response of the all of the calibration cavities (350a, 350b, 350c, 350d) as illustrated in FIG. 7.

Figure 8:
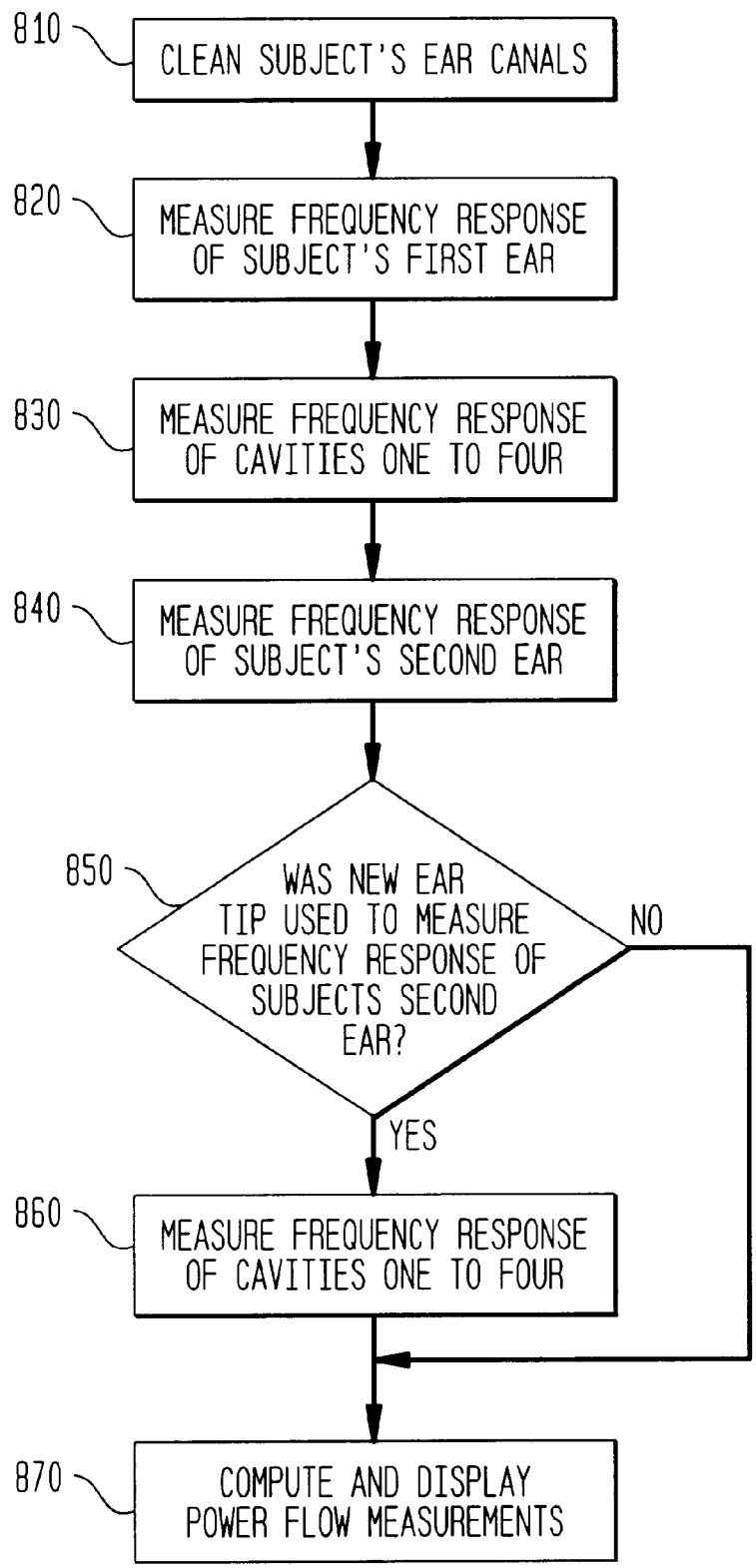
FIG. 8 illustrates the steps for obtaining the power flow measurements of a subject's ears.
Figure 9:
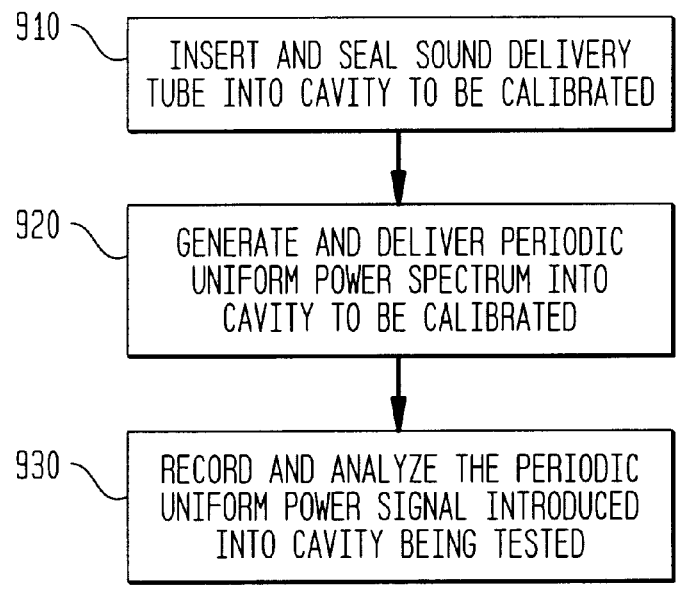
FIG. 9 illustrates the steps for calibrating a receiver within a cavity.

FIG. 8 describes the steps involved in a clinical diagnosis of a subject's ear canals. First, the test equipment is set up. The setup consists of configuring a digital signal processing (DSP) board on a local computer. Probe cable 410 is directly connected to the DSP board. The computer is switched on and the flow measurement application is started. As will be described later, the flow measurement application will receive data from probe 400 and convert it into multiple frequency, impedance, reflectance, and transmitted power measurements.

Next, the subject or individual being tested has his or her ear canals checked for obstructions and cleared under otoscope observation. Probe head 420 having a suitable eartip 440 attached thereto is inserted into the subject's ear canal. A suitable earphone is one that is large enough to seal the ear canal completely. The probe 400 should be inserted as deep into the ear canal as is comfortable for the subject. Generally, the foam tips of the earphones are made of a flexible material that can be squeezed tight prior to insertion. Then, after it has been inserted, the eartip will expand back to its original shape thereby providing a good seal. Each eartip is of a different but known size which is important to record for later calculation of Thevenin parameters.

The pressure frequency response of the subject's ear canal is then measured 820. The subject is asked to remain quiet for a few seconds with their mouth slightly open so as to avoid having measurements altered by subtle muscle clenches around the ear. A periodic signal having a uniform power spectrum is generated and delivered into the ear canal. The periodic signal may be a chirp, swept sinusoids, or noise. The uniform power spectrum is at the transmitter or at the output of the sound delivery tube 450 thereby creating a point source spreading mass of sound pressure. The inserted probe 400 then determines the frequency response of the ear canal by having the microphone 470 transmit the data it picks up via probe cable 410 to the DSP board. It only takes a few seconds to obtain a frequency response. The frequency response is then analyzed and displayed to determine if there are any leaks in the seal between the foam tip and ear canal. An obvious indication of a leaky seal is a sharp notch present on the displayed results between 100 Hz and 300 Hz or low pressure below 300 Hz. If a leaky seal is discovered then the probe must be reinserted and the test performed again. Another source of error to be avoided is excessive handling of the probe cable 410. Even slight disturbances to the probe cable 410 can result in errors due to this noise.

The next step is to measure the frequency responses for each of the calibration cavities 830. There are four calibration cavities in the preferred embodiment although there can be as little as two. Additional cavities provide greater accuracy but the increased accuracy effect is negligible compared to the work required when more than four cavities are employed. The cavity frequency response is measured in the same manner as was the subject's ear. Probe 400, connected to earphone 440 and resting upon probe head rest bar 330, is inserted into bore 340a of the L-shaped stand corresponding with the zero position, $L_0$, until the probe cannot be inserted any further. Cylinder 320 is rotated to one of the four cavity positions and a periodic signal is inserted into the calibration cavity and the frequency response is measured. This is repeated for each cavity. Again, it is critical to provide a leak free seal in order to obtain accurate frequency measurements.

The subject's other ear is next measured for frequency response 840 in the exact manner as his or her first ear. If for any reason the ear tip had to be changed 850 for the second ear then the new tip must also be measured 860 in the calibration cavities. Otherwise, if the same tip was used to measure both ears then the cavity calibration step need only be performed once. We now have frequency response readings for both of the subject's ears and for each of the four calibration cavities.

Once the tester enters the size or type of the foam eartips, a pre-existing datafile is accessed for the mean acoustic length of the cavities $\mathcal{L}_0$, the four differential cavity lengths, ($\Delta_i$=Li−$\mathcal{L}_0$,i =1,2,3,4), the diameter of the test cavities D, and the spreading mass $M_s$. These seven parameters are then used to initialize a gradient search for new values of $\mathcal{L}_0$ and $M_s$. The frequency response measurements for the calibration cavities are converted into the source transducer's open circuit pressure $P_s(\omega)$ and source impedance $Z_s(\omega)$. These two responses along with the pressure response measured in the subject's ear canal are sufficient to compute the subject's ear canal impedance and/or reflectance.

An important consideration in the design of the instrument is the use of reflectance rather than impedance in deriving acoustic power flow. Reflectance is used for two main reasons. First, reflectance has a direct interpretation in terms of relative power flow from a measurement perspective. Second and more important, acoustic impedance does not provide a complete description of a one-port system (e.g. eardrum impedance). Knowledge of eardrum impedance, for instance, fails to distinguish between incident and retrograde power flows since impedance only describes the difference between them, i.e. incident-reflected Thus, impedance is an incomplete description of the power transfer function (transmitted/incident) for a one-port system. Pressure reflectance, however, defines a power transfer function in terms of both magnitude and phase. This definition requires the additional concept of a power delivery system described by a dispersionless transmission line having a characteristic impedance ($Z_0$) and velocity (c) loaded with energy having a spectral ($\omega$) and spatial ($\chi$) composition according to:

$$\frac{|P_+(\omega, x/c - t)|^2}{z_0}$$

where $P_+$ is the forward traveling pressure wave on the transmission line, $\omega$ is angular frequency, $\chi$ is the position along the transmission line, and t is time.

The available power $\Pi_+$ is defined in terms of a forward traveling pressure wave $P_+$ in the ear canal as the power traveling toward the tympanic membrane according to:

$$\Pi_+ = \frac{|P_+(\omega)|^2}{z_0}$$

where $z_0$=$\rho$c/A is the characteristic impedance of the ear canal, $\rho$ is the density of air, c is the speed of sound, and A is the cross-sectional area of the ear canal. Similarly, the retrograde or backward traveling power II. due to reflections and non-linear cochlear mechanisms is:

$$\Pi_- = \frac{|P_-(\omega)|^2}{z_0}$$

The ratio of the retrograde to incident pressure defines pressure reflectance as:

$$R(\omega) \equiv \frac{P_-(\omega)}{P_+(\omega)}$$

and its square magnitude defines the power reflectance as:

$$|R(\omega)|^2 = \frac{\Pi_-}{\Pi_+}$$

and the relative absorbed power is:

$$\frac{\Pi_A}{\Pi_+} \equiv \frac{\Pi_+ - \Pi_-}{\Pi_+} = 1 - |R(\omega)|^2$$

The normal ear absorbs power from about 800 Hz to 8 kHz. When the relative power absorbed $\Pi_A/\Pi_-$ is less than some threshold, 0.25 for instance, the ear or middle ear are disfunctional. Typical values for the relative power absorbed are greater than 0.75. Any values below this norm indicates a pathology, the severity of which depends upon the ratio of power absorbed.

Another particularly useful application of the above derived measurements, aside from diagnosing ear pathologies, is in accurately calibrating and setting hearing aids for individuals who require them. Individuals that rely on hearing aids can have the acoustic power flow measured in their ears to determine how to precisely adjust the hearing aid device. Using the foregoing system and method provides hearing aid users with a way of optimizing their hearing aid devices.

An alternative calibration device design is shown in FIGS. 11–14. The reason for this is to accommodate eartips of different sizes. Thus, the device works for infants (very small eartips) to children (small earphones) to adults (larger earphones).

Figure 11:
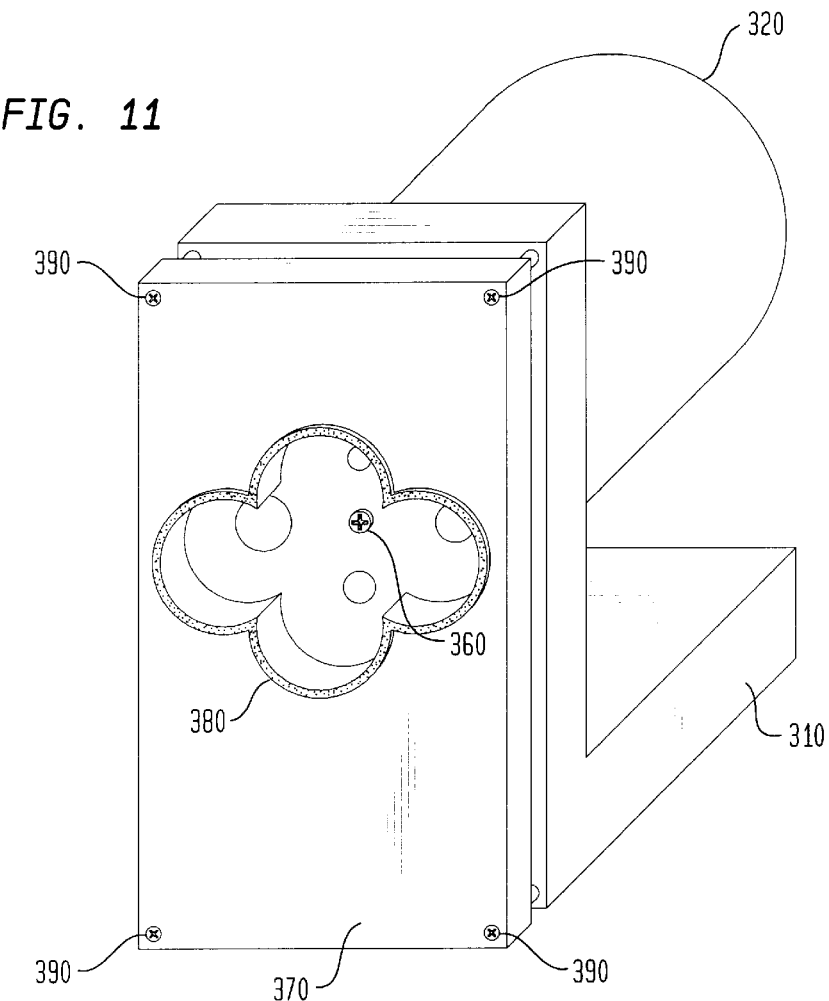
FIG. 11 illustrates a calibration device according to an alternate embodiment of the invention.

FIG. 11 shows a calibration device similar to that shown in FIG. 3. This one, however, has an additional face plate 370 attached to the upright portion of stand 310 by four screws 390, one in each corner. Face plate 370 has a "four leaf clover" like cutout portion surrounded by a padded material 380. Each "leaf" of the clover is designed to receive the probe/earphone combination. The padded material 380, preferably rubber, is for holding the probe 400 in place during the calibration process.

Figure 12:
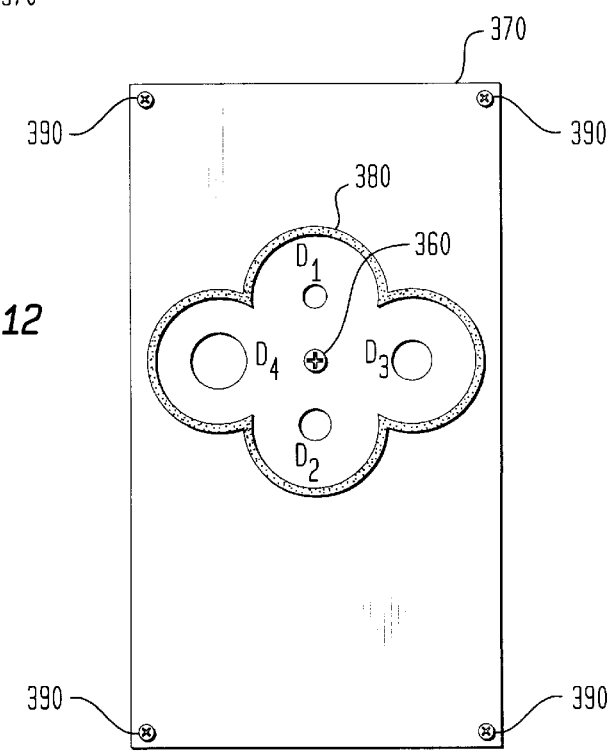
FIG. 12 is a front view of the calibration device of FIG. 11.
Figure 13:
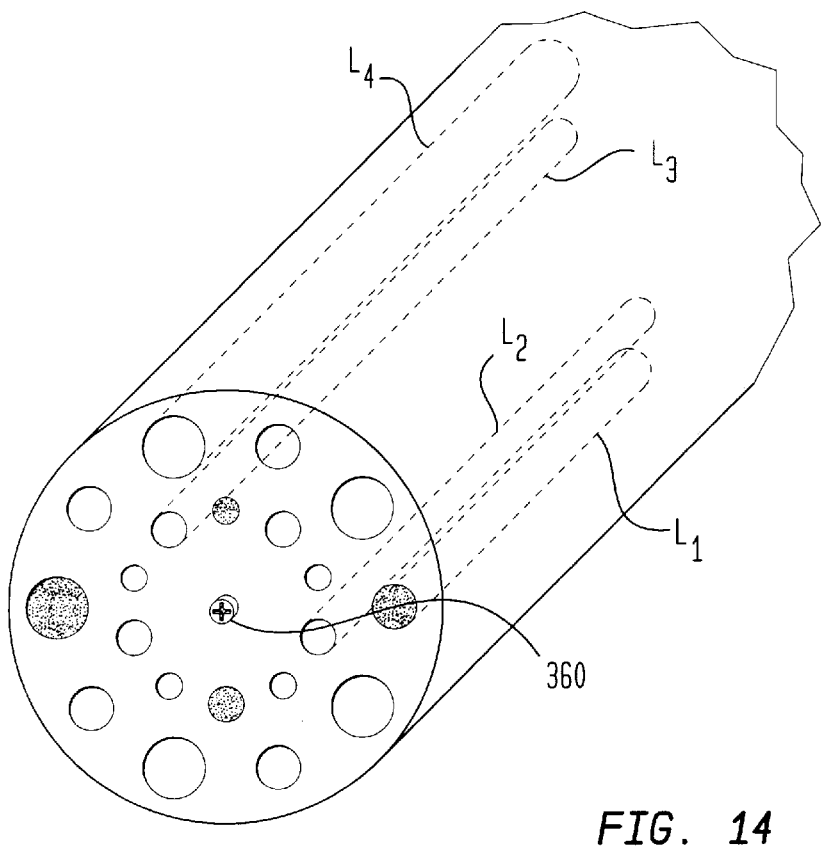
FIG. 13 illustrates a perspective view of the calibration device cylinder apart from the rest of the calibration device.
Figure 14:
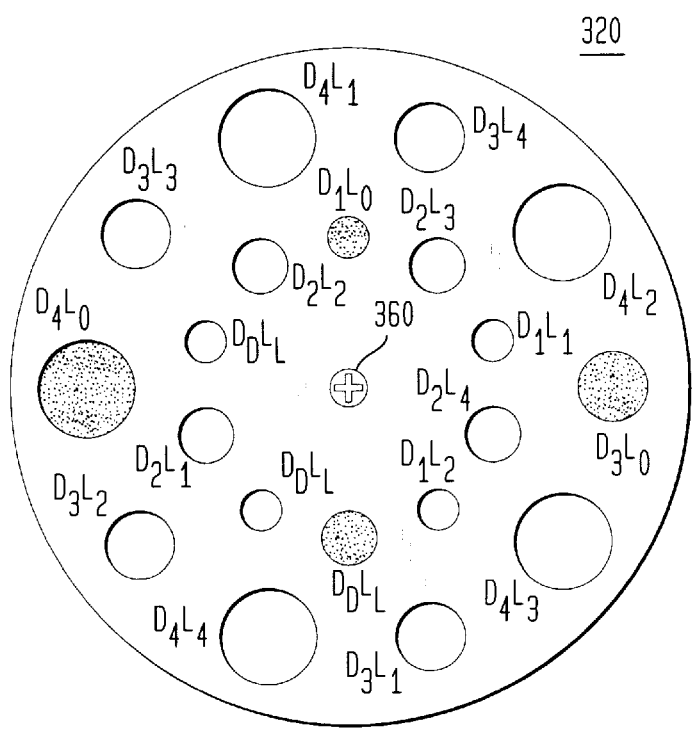
FIG. 14 is a front view of the cylinder shown in FIG. 13.

FIG. 12 is a front view of FIG. 11. Four holes of varying diameter ($D_1$, $D_2$, $D_3$, $D_4$) are shown in the upright portion of stand 310. Screw 360 still serves as the mechanism that connects cylinder 320 to stand 310 allowing the cylinder to rotate. The first pair (smaller diameter) of holes, $D_1$ and $D_2$, share a concentric circle within cylinder 320 while the second pair (larger diameter) of holes, $D_3$ and $D_4$, share a slightly larger concentric circle within cylinder 320. These concentric circles are readily apparent when viewing FIGS. 13–14. FIG. 13 is a perspective view of the cylinder attachment apart from the rest of the calibration device. Cylinder 320 is rotatable such that each of the four holes ($D_1$, $D_2$, $D_3$, $D_4$) in the upngnt portion of stand 310 can be aligned with five respective cylinder positions ($L_0$, $L_1$, $L_2$, $L_3$, $L_4$). Thus, one would need four separate calibration devices like that illustrated in FIG. 3 to achieve the results of the one calibration device illustrated in FIG. 11.

The present invention provides many significant advantages over the prior art. First, acoustic intensity absorbed in the middle ear can be measured directly in a simple easy to use instrument. Second, the measurement of acoustic intensity eliminates problems associated with variable acoustic impedance within the middle ear. Third, variability in hearing level measurement in adult ears having normal middle ear finction is reduced by reducing calibration variability due to inter-subject differences in acoustic impedance. Fourth, errors in measuring childrens' and infants' ears as well as middle ear pathologies are reduced. Fifth, relatively accurate measurements of sound power reaching the cochlea over a wide frequency range (i.e. 40–12,000 Hz) can be obtained. Lastly, all of the above objectives can be obtained at significant cost and time savings than is currently possible. Results are returned in approximately two to three minutes as opposed to the three to four hours typical of prior art ABER systems.

What is claimed is:

1. A system for measuring the acoustic power flow in an ear canal comprising:

a signal processor;

a probe terminating in a probe tip comprising a microphone and a receiver source transducer electrically connected to said signal processor;

an eartip removably connectable to said probe and adapted to receive said source transducer, said eartip being made of a soft resilient material for providing an airtight seal between said probe and said ear canal, said earphone further comprising a sound delivery tube extending along its axis for relaying a periodic signal into said ear canal; and a calibration device comprising an L-shaped base and stand configuration having a circular bore, and a cylinder extending outward from said stand having a plurality of unequal length cavities which are parallel to its axis, and screw means extending the length of the cylinder axis into and through said stand for fastening said cylinder to said stand and allowing said cylinder to rotate about its axis;

a probe head rest bar extending across said stand and having a partial cut out semi-circular portion aligned with said circular bore in said stand for receiving and securing said probe within said circular bore, wherein said probe is inserted into said ear canal and a periodic signal is introduced into said ear canal via said transducer for measuring and relaying said ear canal's frequency response to said signal processor, said probe is then inserted into each calibration cavity and a periodic signal is introduced into each said calibration cavity for measuring and relaying each said calibration cavity's frequency response to said signal processor where said signal processor calculates the acoustic power flow of said ear canal utilizing said measured ear canal frequency response and said calibration cavity frequency responses.

2. A method for measuring the acoustic power flow in a human ear canal comprising the steps of:

a. measuring the frequency response of a subject's ear canal by introducing a periodic signal from a source transducer into said ear canal and recording the frequency response of same;

b. measuring the frequency response of a plurality of cavities having known geometries by introducing said periodic signal from said source transducer into said cavities and recording the frequency response of same by a receiving transducer;

c. converting the measured frequency responses of the subject's ear canal and the measured frequency of said plurality of cavities into the source transducer's open circuit pressure $P_s(\omega)$ and source impedance $Z_s(\omega)$;

d. determining the available power $\Pi_+$ in the ear canal according to:

$$\Pi_+ = \frac{|P_+(\omega)|^2}{z_0}$$

where $P_+$ is the forward traveling pressure wave in the ear canal traveling toward the tympanic membrane, $\Pi$ is the angular frequency, and $Z_0$ is the characteristic impedance of the ear canal calculated according to $Z_0 = \rho c/A$ where $\rho$ is the density of air, c is the speed of sound, and A is the cross-sectional area of the ear canal;

e. determining the retrograde power $\Pi$ in the ear canal according to:

$$\Pi_- = \frac{|P_-(\omega)|^2}{z_0}$$

where

P is the backward traveling pressure wave in the ear canal, $\omega$ is the angular frequency, and $Z_0$ is the characteristic impedance of the ear canal calculated according to $Z_0 = \rho c/A$ where $\rho$ is the density of air, c is the speed of sound, and A is the cross-sectional area of the ear canal;

f. determining pressure reflectance as:

$$R(\omega) \equiv \frac{P_-(\omega)}{P_+(\omega)}$$

g. determining power reflectance as:

$$|R(\omega)|^2 = \frac{\Pi_-}{\Pi_+}$$

h. determining the relative absorbed acoustic power flow in the ear canal as:

$$\frac{\Pi_A}{\Pi_+} \equiv \frac{\Pi_+ - \Pi_-}{\Pi_+} = 1 - |R(\omega)|^2.$$

3. The method of claim 2, wherein the converting step (c) further comprises searching for the spreading mass.

4. The method of claim 2, wherein the converting step (c) further comprises searching for the mean acoustic length of the cavities.

5. The method of claim 2, wherein the converting step (c) fiuther comprises simultaneously searching for the spreading mass and mean acoustic length.

6. The method of claim 2, wherein the converting step (c) further comprises simultaneously searching for the lengths of each of the cavities and the spreading mass.

7. A system for measuring the acoustic power flow in a cavity comprising:

signal processor means;

probe means connected to said processor means;

cavity calibration means having
- a plurality of unequal length calibration cavities,
- eartip means removably connectable to said probe means, said eartip means comprising a soft resilient material for providing an airtight seal between said probe means and said cavity, and between said probe means and said calibration cavities, and between said probe means and said calibration cavities, said eartip means further comprising sound delivery tube means extending along the axis of said eartip means for relaying said periodic signal into said cavity or into said calibration cavities; and
- heating means for maintaining the calibration cavities at a substantially constant temperature roughly equivalent to human body temperature;

wherein
said probe means is inserted into said cavity and a periodic signal is introduced into said cavity via said probe means for measuring and relaying said cavity's frequency response to said signal processor means, said probe means is then inserted into each calibration cavity and a periodic signal is introduced into each of said calibration cavities for measuring and relaying each said calibration cavities for measuring and relaying each said calibration cavity's frequency response to said signal processor means, and said processor means calculates the acoustic power flow of said cavities utilizing said measured cavity frequency response and said calibration cavity frequency responses.

8. The system of claim 7 wherein said probe means terminates in a probe tip, said probe tip comprising a source transducer of a microphone and a pair of receivers electrically connected to said processor means.

9. The system of claim 8, wherein said eartip sound delivery tube means is adapted to receive said source transducer.

10. The system of claim 7, wherein said heating means are a plurality of heating elements proximal to said calibration cavities for maintaining the calibration cavities at a substantially constant temperature roughly equal to human body temperature.

11. The system of claim 10, wherein said calibration cavities have hard walls.

12. The system of claim 10 wherein said calibration cavities terminate in known impedances.

13. The system of claim 7, wherein said signal processor means is a digital signal processor.

14. The system of claim 7, wherein said cavity is a human ear canal.

15. The system of claim 7, wherein a microphone is part of said probe means.

16. The system of claim 15, wherein said calibration cavities terminate in known impedances.

17. The system of claim 7, wherein said calibration cavities have hard walls.

* * * * *